United States Patent

Runciman et al.

Patent Number: 5,746,742
Date of Patent: May 5, 1998

[54] BONE PLATE TEMPLATE

[75] Inventors: Robert John Runciman, Renfrew, Canada; Randall N. Allard, Plymouth, Ind.

[73] Assignees: Bristol-Myers Squibb Company, New York, N.Y.; Terray Corporation, Ontario, Canada

[21] Appl. No.: 668,299

[22] Filed: Jun. 25, 1996

[51] Int. Cl.[6] .................................................. A61B 17/56
[52] U.S. Cl. ............................ 606/69; 606/70; 606/71
[58] Field of Search ................................ 606/69, 70, 71, 606/101, 102

[56] References Cited

U.S. PATENT DOCUMENTS

| | | |
|---|---|---|
| 4,573,458 | 3/1986 | Lower. |
| 5,372,598 | 12/1994 | Luhr et al. .................. 606/69 |
| 5,487,741 | 1/1996 | Maruyama et al. .......... 606/69 |

OTHER PUBLICATIONS

"Bone Plates," Vitallium Surgical Appliances, Catalog No. 6321, 3/48, p. 7.
"ECT Internal Fracture Fixation Systems" catalogue, Zimmer, Inc., 1987, pp. C28–C35 plus front and back covers, see particularly p. C28.
Photographs A, B and C show Zimmer, Inc., pelvic bone plate, Catalogue No. 1179, 1987.
Photographs D, E and F show Zimmer, Inc., pelvic bone plate template, Catalogue No. 1179-30, 1987.
"Internal Fracture Fixation Systems", catalog extract re 2371-5,7,9 Bending Templates and 1179-30 Pelvic Plate Templates, Zimmer, Inc., 1987, pp. C60–C61 plus front and back covers.
"Forte Distal Radial Plate System", catalog extract re Plate Application, Zimmer, Inc., 1994, p. 5 plus front and back covers.
"Instruments for Plates", catalog extract re Bending Templates, Synthes, 1987, pp. 3–13.

*Primary Examiner*—Michael Buiz
*Assistant Examiner*—Julian W. Woo
*Attorney, Agent, or Firm*—Pearne, Gordon, McCoy & Granger LLP

[57] ABSTRACT

A template is disclosed for use in preparing a contouring model for a bone plate to be implanted on a bone. The bone plate is the type comprising an elongated strip having at least two screw holes formed therein, adjacent screw holes being joined together by unapertured regions of the elongated strip. The template has a silhouette substantially resembling a selected bone plate, with first portions corresponding to the locations of the screw holes. The first portions are bridged by second portions corresponding to the locations of the unapertured regions of the strip. The second portions are of reduced width relative to a corresponding unapertured region of the bone plate, whereby the template is deformable in the region of the second portions by manual pressure.

18 Claims, 1 Drawing Sheet

BONE PLATE TEMPLATE

The present invention relates to the field of orthopaedic tools and instruments. In particular, the present invention provides a novel template for use during procedures involving the fitting and implantation of bone plates.

A bone plate is a plate that is fastenable to the surface of a bone to immobilize a fracture thereof, or to immobilize a reconstructed area thereof. The plate is made from a strip of metal such as surgical grade stainless steel, or titanium, having very high tensile strength. It is provided along its length with a series of screw holes, to permit the plate to be affixed to a bone by the use of surgical screws. Before a bone plate is affixed to the surface of a bone, however, it must be contoured to match the natural or desired reconstructed shape of the bone surface. Such contouring is classifiable as bending, arcing, or twisting. Bending is displacement about one or more axes perpendicular to the central longitudinal axis of the plate and parallel to the planes of the top and bottom surfaces of the plate (considering the plate as being flat, even though it may be slightly curved from side to side to present a concave underside). Arcing is displacement about one or more axes perpendicular to the central longitudinal axis of the plate and perpendicular to the said planes of the top and bottom surfaces of the plate. Twisting is displacement rotationally of a portion of the plate, relative to another portion of the plate, about the central longitudinal axis of the plate.

It is known in the art of bone plate design to provide inwardly directed notches between the holes to facilitate shaping of the plate. These notches lessen the amount of material between the holes, and thereby tend to redistribute the stiffness of the plate along its length. Force applied to the plate to effect a shaping thereof will tend not to concentrate in the region of the holes, but can be equalized along the length of the plate, or concentrated in the spaces between the holes as desired. To avoid contouring a plate slowly and gradually by trial and error, fitting and re-fitting the plate against a bone in an open surgical situation, a clinician may use a template.

A bone plate template is an easily contourable plate that is placed against a bone, and contoured using finger pressure. After it is contoured by a clinician, it is used by a technician to create a duplicate contoured bone plate for implantation. The template must, therefore, resemble its corresponding bone plate in all material aspects. Therefore, most templates are simply a silhouette of their corresponding bone plate. Such prior art templates, made from a relatively soft material such as aluminum, may still require substantial force to deform, especially to arc, which is not desirable in a confined surgical environment.

Moreover, it has been observed that when soft material such as aluminum is used in a template, attempts at arcing may result in folding or kinking of the template, in the notch region. The applicant has determined that this particular phenomena tends to disappear if the width to thickness ratio of the material of the material of the template is kept below about 1.6:1, preferable about 1.5:1, but as low as about 1.4:1.

Accordingly, it is an advantage of the present invention to provide a bone plate template which is easily and reliably shaped by hand.

Using a material with no appreciable spring to it, such as 1100-0 aluminum, the applicant has produced a template for a bone plate exhibiting substantially the silhouette of the bone plate, but with notches between the screw holes having reduced width relative to the corresponding notch portion on the bone plate. Such a template can be easily formed with finger and hand pressure to any desired contour, for use by a technician in the contouring of a bone plate for implantation.

In a broad aspect, therefore, the present invention relates to a template for use in preparing a contouring model for a bone plate to be implanted on a bone said bone plate comprising an elongated strip having at least two screw holes formed therein, adjacent screw holes being joined together by unapertured regions of said elongated strip; said template having a silhouette substantially resembling a selected said bone plate, with first portions corresponding to the locations of said screw holes being bridged by second portions corresponding to the locations of said unapertured regions of said strip, said second portions being of reduced width relative to a corresponding unapertured region of the bone plate, whereby said template is deformable in the region of said second portions by manual pressure.

In another broad aspect, the present invention relates to a template for use in preparing a contouring model for a bone plate, wherein an upper or a lower surface of the template is embossed with a recognizable indicia.

In drawings that illustrate the present invention by way of example:

Figure 1:
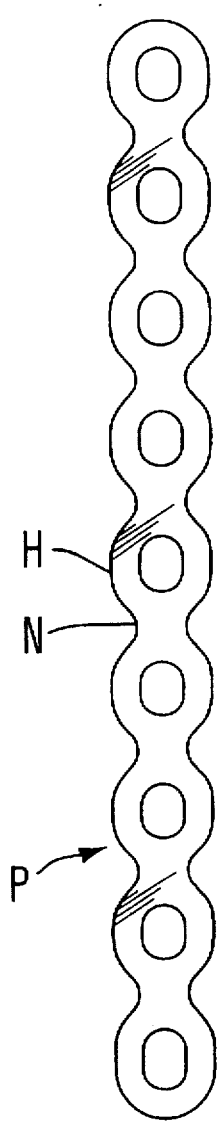
FIG. 1 is a plan view of a known bone plate.

Referring now to FIG. 1, a bone plate P can be viewed as a series of screw hole regions H linked together by a series of un-apertured notch regions N. Shaping of the bone plate implant is typically accomplished using instruments and tools permitting fine control of the process. However, shaping of the bone plate template is typically accomplished manually.

Figure 2:
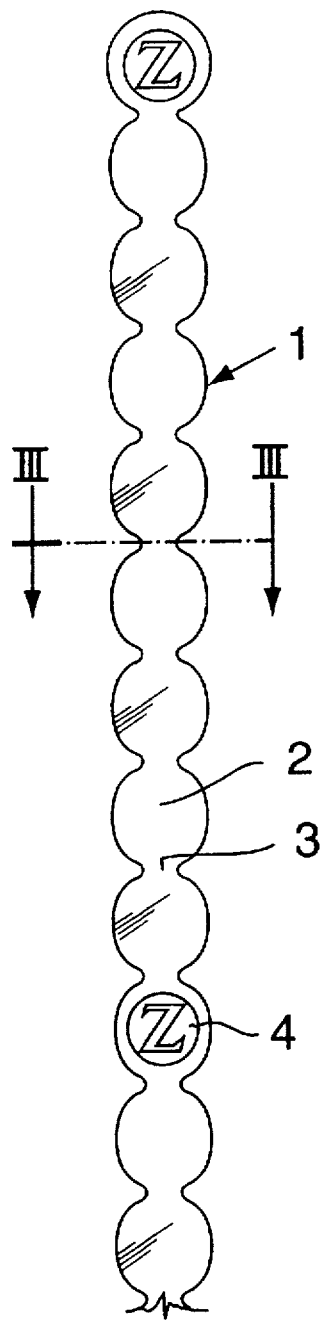
FIG. 2 is a partial plan view of a template according to the present invention for use with the bone plate of FIG. 1.
Figure 3:
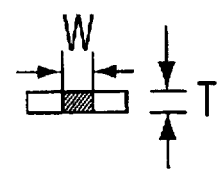
FIG. 3 is a cross-section view of the template of FIG. 2, through line III—III.

Referring now to FIGS. 2 and 3, the applicant has constructed a template 1 composed of a series of rounded flat zones 2, each resembling in silhouette the screw hole area of a given bone plate. These are joined by short, inwardly restricted connecting sections 3, each as long as, but considerably narrower than, the notched portion of a corresponding bone plate. As is typical with bone plate templates, the template 1, as shown in FIG. 2, does not include holes corresponding to the holes in the bone plate P.

Referring to FIG. 3, it will be observed that the width W of each short connecting section 3 is about 1.5 times the thickness T of the template. The applicant has determined that such width W may be up to about 1.6 times the thickness T of the template, and is preferably from about 1.4 to about 1.6 times the thickness T. It will be observed, however, from a comparison of FIGS. 1 and 2, that except for the narrowing of the notch section 3 in the template 1, the template 1 has a silhouette substantially identical to the bone plate P. The narrowing of the notch on the template provides a template 1 in which the notch section 3 has a reduced width relative to the corresponding unapertured region N of the corresponding bone plate P. The reduced width of the notch sections 3 of the template 1 may be reduced, for example, by at least about 15% relative to the corresponding unapertured region of the corresponding bone plate P, depending on the overall width of the plate and template. Two examples of this relative reduction are given for reference, but are not intended to be exhaustive or to limit the invention in any way. In the first example, the bone plate P and corresponding template 1 may each have an overall width of 0.315 inches. The width of the notch N of plate P may be 0.145 inches, while the notch width W of template 1 may be 0.110 inches, a decrease of 24% in width. In the second example, the bone plate P and corresponding template 1 may each have an overall width of 0.394 inches. The width of the notch N of plate P may be 0.205 inches, while the notch width W of the template 1 may be 0.124 inches, a decrease of 40% in width. Accordingly, when the template is bent, twisted and arced as appropriate to obtain a desired contour, the clinician will be assured that a bone plate similarly contoured will fit in the identical manner as the template against the bone. The template of the present invention allows sufficient even and straight force to be manually applied to the template in order to shape the template by bending, arcing or twisting without undesirable deformation or folding of the template.

In order to assist in orientation of a template, so that a bone plate is not contoured upside down, or in reverse, it is conventional for one end, say the intended distal end, of a bone plate to be provided with an aperture. To tell top from bottom, the plate is etched with a logo, name, lot number or the like. It will be appreciated, however, that an etched marking is easily obscured with blood, and therefore, plates are frequently incorrectly contoured because of lapses in communication or understanding caused by the obscuring of easily obscured markings. The template of the present invention provides an improved feature for orienting the template by providing an embossed mark or indicia 4 on a selected one of the upper or lower surfaces of the template, at a selected one of the intended distal or proximal ends thereof. The mark is preferably the trademark or logo of the manufacturer of the template and its corresponding bone plate, so that the template is easily and accurately matched to its corresponding bone plate, although any suitable recognizable indicia may be used. Moreover, in a preferred embodiment more than one such embossed mark is made on the template spaced apart by a desired number of zones 2, corresponding to the length of a known bone plate, whereby a clinician can merely cut off a portion of a longer template, if desired, to obtain a shorter usable template. The embossing (after a quick wipe with a finger) allows the surgeon to readily identify the markings, even in a surgical environment, to confirm orientation of the template.

The template may be made from any suitably soft metal that exhibits negligible spring and sufficient stiffness to hold its form after contoured, so as to be useful as a model for the contouring of a bone plate. It must not, for instance, bend under its own weight if held at one end. The applicants have found that 1100-0 aluminum is a suitable material, and it is expected that other suitable materials will be apparent to those skilled in the art.

The above description is not meant to limit the present invention. It is anticipated that numerous variants will be obvious to one skilled in the art. In particular, the applicants have described a template suitable for use with a particular bone plate. Other bone plates exist, and it is expected that the present invention can be adapted for use with them, without the further exercise of inventive ingenuity, with such adaptions being entirely within the scope of the substance of this invention.

We claim:

1. In combination, a template and a corresponding bone plate, the template for use in preparing a contouring model for the bone plate to be implanted on a bone, said bone plate comprising an elongated strip having at least two screw holes formed therein, adjacent screw holes being joined together by unapertured regions of said elongated strip; said template having a silhouette substantially resembling a selected said bone plate, with first portions corresponding to the locations of said screw holes being bridged by second portions corresponding to the locations of said unapertured regions of said strip, said template has a thickness T, and said second portions have a minimum width W, the ratio of W:T being from about 1.4:1 to about 1.6:1, whereby said template is deformable in the region of said second portions by manual pressure, said first portions lacking apertures corresponding in size to said screw holes.

2. The combination as claimed in claim 1, wherein said ratio of W:T is about 1.5:1.

3. The combination as claimed in claim 2, made from grade 1100-0 aluminum.

4. The combination as claimed in claim 1, wherein the first portions have a width which is wider than the width W of the second portions.

5. The combination as claimed in claim 1, wherein the width W of the second portions of the template is reduced relative to a corresponding unapertured region of the bone plate.

6. The combination as claimed in claim 5, wherein the reduced width of the second portions is reduced by about at least 15% relative to the corresponding unapertured region of the bone plate.

7. The combination as claimed in claim 5, wherein the reduced width of the second portions is reduced by from about 15% to about 40% relative to the corresponding unapertured region of the bone plate.

8. The combination as claimed in claim 5, wherein the reduced width of the second portions is reduced by about 24% relative to the corresponding unapertured region of the bone plate.

9. The combination as claimed in claim 1, wherein an upper or a lower surface of at least one of said first portions is embossed with a recognizable indicia.

10. The combination as claimed in claim 9, wherein the upper surface of a said first portion at one end of said template is embossed with a said recognizable indicia.

11. The combination as claimed in claim 10, wherein the upper surface of another said first portion, spaced from said end of said template by a space corresponding to a predetermined number of screw holes on a bone plate is embossed with a said recognizable indicia.

12. The combination as claimed in claim 11, wherein said space corresponding to a predetermined number of screw holes corresponds to the length of a selected bone plate.

13. The combination as claimed in claim 9, wherein said recognizable indicia is a trademark, corresponding to the trademark associated with said bone plate.

14. In combination, a template and a corresponding bone plate, the template for use in preparing a contouring model for the bone plate to be implanted on a bone, said bone plate comprising an elongated strip having at least two screw holes formed therein, adjacent screw holes being joined together by unapertured regions of said elongated strip; said template having a silhouette substantially resembling a selected said bone plate, with first portions corresponding to the locations of said screw holes being bridged by second portions corresponding to the locations of said unapertured regions of said strip, said first portions lacking apertures corresponding in size to said screw holes, wherein the upper surface of one of said first portions of the template is embossed with a first recognizable indicia at a first location at one end of said template and the upper surface of another portion of said template, spaced apart from said first location a distance corresponding to a predetermined number of screw holes on said bone plate, is embossed with a second said recognizable indicia.

15. The combination as claimed in claim 14, wherein said distance corresponding to a predetermined number of screw holes corresponds to the length of a selected said bone plate.

16. The combination as claimed in claim 15, wherein first recognizable indicia is a trademark, corresponding to the trademark associated with said bone plate.

17. The combination as claimed in claim 14, wherein said another portion is another first portion.

18. The combination as claimed in claim 17, wherein said first recognizable indicia is a trademark, corresponding to the trademark associated with said bone plate.

* * * * *

UNITED STATES PATENT AND TRADEMARK OFFICE
CERTIFICATE OF CORRECTION

PATENT NO. : 5,746,742
DATED : May 5, 1998
INVENTOR(S) : Robert John Runciman, et al.

It is certified that error appears in the above-identified patent and that said Letters Patent is hereby corrected as shown below:

Col. 4, line 3, after "strip," insert --wherein--.

Col. 5, line 4, after "wherein" insert --said--.

Signed and Sealed this

Twenty-seventh Day of October, 1998

Attest:

BRUCE LEHMAN

*Attesting Officer*    *Commissioner of Patents and Trademarks*